US00PP35222P2

(12) United States Plant Patent
Hansen

(10) Patent No.: US PP35,222 P2
(45) Date of Patent: Jun. 13, 2023

(54) ***PHLOX* PLANT NAMED 'SUNSET CORAL'**

(50) Latin Name: *Phlox paniculata*
Varietal Denomination: Sunset Coral

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,683

(22) Filed: Oct. 13, 2022

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./263.1, 320
See application file for complete search history.

*Primary Examiner* — Karen M Redden

(57) ABSTRACT

A unique cultivar of Tall *Phlox* plant named 'Sunset Coral' characterized by vigorous, dense, upright, multi-stemmed, winter-hardy habit with dark-green, lanceolate leaves. Flowering begins in late July and continuing for up to five weeks in cooler weather conditions, on heavily-branched peduncles, and completely cover the top of the plant in peak season. Petals are coral-pink with a tinge of orange, with the orange coloration more intense in cooler conditions. The new plant shows excellent powdery mildew resistance. The new plant is especially suitable for a cut flower, for the landscape as a potted plant and in the garden as a specimen or en masse.

2 Drawing Sheets

Botanical classification: *Phlox paniculata.*
Variety denomination: 'Sunset Coral'.

STATEMENT REGARDING PRIOR DISCLOSURES UNDER 37 CFR 1.77(b)(6)

The first non-enabling information of the claimed plant, in the form of a photograph and brief description on a website operated by Walters Gardens, Inc. on Dec. 1, 2021. Walters Gardens, Inc. also listed the new plant in their "Walters Gardens 2022-2023 Catalog" initially going out to customers on Jun. 8, 2022. Walters Gardens, Inc. obtained the plant and all information relating thereto, from the inventor. No plants of *Phlox* 'Sunset Coral' have been sold publicly in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Tall *Phlox* plant known as *Phlox* 'Sunset Coral' and will be referred to hereafter by its cultivar name, 'Sunset Coral', or the "new plant". The new plant was hybridized by the inventor at a wholesale perennial nursery in Zeeland, Mich. on Aug. 5, 2013, as a cross between *Phlox paniculata* 'Barsixtytwo' U.S. Plant Pat. No. 22,234 as the female or seed parent and 'Glamour Girl' U.S. Plant Pat. No. 25,778 as the male or pollen parent. The new plant passed initial evaluation on Aug. 5, 2013, and was assigned the breeder code 13-308-1 through the remaining evaluation process. 'Sunset Coral' was first asexually propagated by stem cuttings in the greenhouses at the same nursery in Zeeland, Mich. in the summer of 2017. The unique characteristics of the new plant have been found to be reproducible and stable in successive generations of asexually propagated and the resultant plants have been found to be identical to the original selection.

BRIEF SUMMARY OF THE PLANT

*Phlox* 'Sunset Coral' is unique from all other Tall *Phlox* known to the inventor. The nearest comparison plants known to the inventor include: the female and male parents, 'Ditomdre' U.S. Plant Pat. No. 20,907, 'Versorange' U.S. Plant Pat. No. 29,594, 'Watermelon Punch' U.S. Plant Pat. No. 19,610, 'Party Punch' U.S. Plant Pat. No. 22,926, 'Windsor' (not patented), and 'Orange Perfection' (not patented).

The female parent has a shorter and more compact habit with a less branched inflorescence, and the flower petals are smaller and of a more purplish hue. The male parent has flowers that are hot coral-pink.

'Ditomdre' has a smaller, shorter habit, the inflorescences are much smaller with fewer flowers, and the flower color is deeper with a different hue. are more cupped and the foliage is more mildew prone. 'Versorange' has a shorter habit with fewer flowers per inflorescence, and the petals are light red-colored. 'Watermelon Punch' has a smaller habit, fewer flowers per inflorescence, and the flowers are more pinkish. 'Party Punch' has a smaller habit, the inflorescences are smaller, and the flowers are more pink. 'Windsor' has flowers that are lighter pink with a much darker pink eye, and the habit is much taller. 'Orange Perfection' has a taller habit with flowers that are a deeper salmon-orange, and is more susceptible to powdery mildew.

*Phlox* 'Sunset Coral' differs from all other *Phlox* known to the inventor in the following repeatedly observed traits in combination:

1. Vigorous plants of dense upright habit, producing medium-tall, clean, dark-green, glabrous, lanceolate leaves;
2. Multiple lightly-branched stems produce heavily-branched panicles;
3. Flower beginning in late July and continuing for up to five weeks, in cool conditions, completely covering plant at peak flowering;
4. Flowers are coral-pink with a tinge of orange, darkest orange under cool temperatures;
5. Foliage is highly resistant to powdery mildew in conditions that would normally be exhibited on partially susceptible cultivars.

BRIEF DESCRIPTION OF THE DRAWINGS

The photographs of the new plant demonstrate the unique traits of *Phlox* 'Sunset Coral' and the overall appearance of the plant at three-years-old growing in a full-sun display garden in Zeeland, Mich. The colors in the drawings are as accurate as reasonably possible with color reproductions. Variation in ambient light spectrum, source and direction may cause the appearance of minor variation in color.

DETAILED BOTANICAL DESCRIPTION

Figure 1:
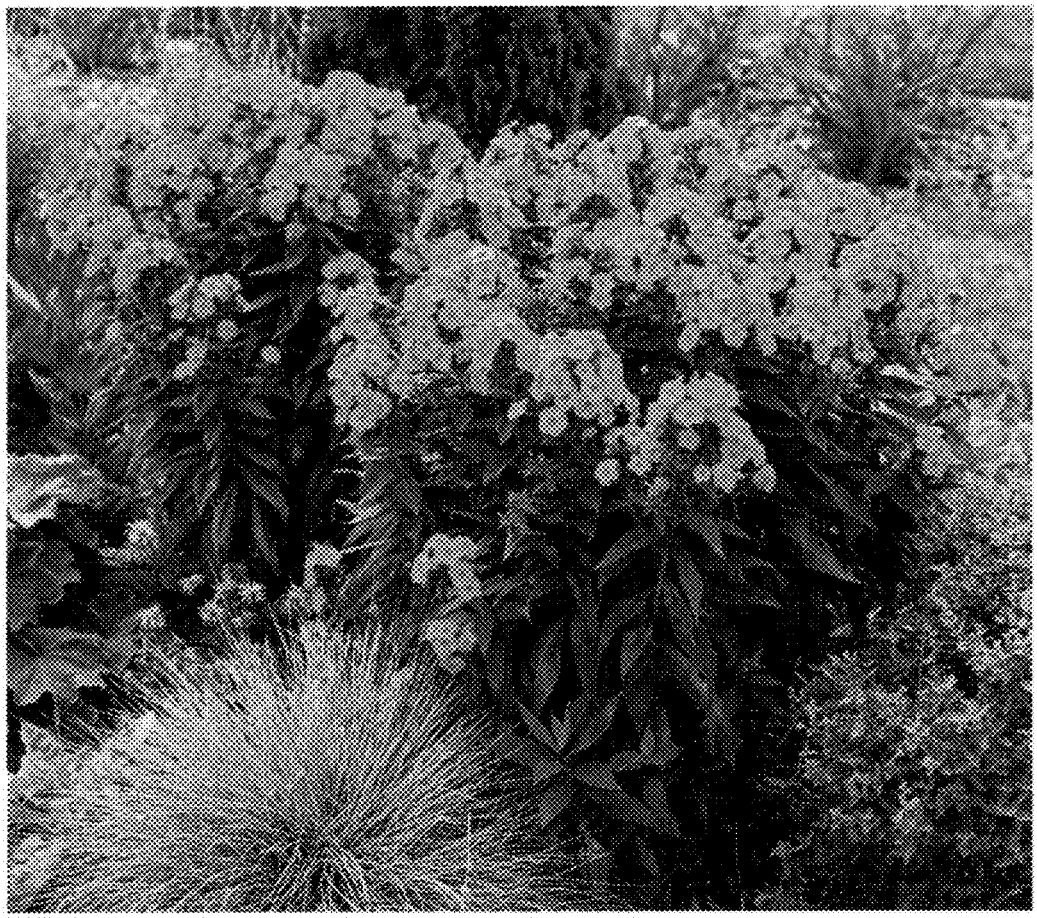
FIG. 1 shows a landscape habit view of the new plant in peak flower.
Figure 2:
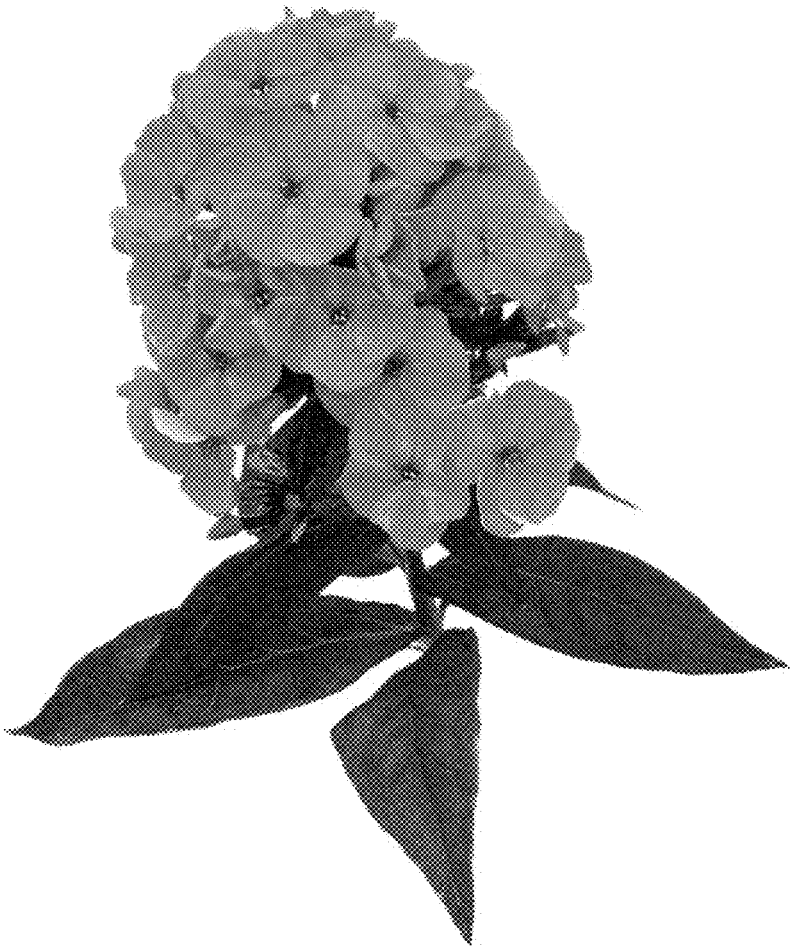
FIG. 2 shows a close-up of the flowers and buds.

The following descriptions and color references are based on the 2015 edition of The Royal Horticultural Society Colour Chart except where common dictionary terms are used. *Phlox* 'Sunset Coral' has not been observed under all possible environments. The phenotype may vary slightly with different growing environments such as temperature, light, fertility, soil pH, moisture, and maturity levels, but without any change in the genotype. The following observations and size descriptions are based on two-year-old plants in a partially shaded greenhouse of a wholesale perennial nursery in Zeeland, Mich. with supplemental fertilizer and water as needed.

Botanical classification: *Phlox paniculata;*

Parentage: Female or seed parent is *Phlox paniculata* 'Barsixtytwo'; male or pollen parent is 'Glamour Girl';

Plant habit: Winter-hardy, evergreen herbaceous perennial; dense, producing about 10 stiff, upright stems; flowering to about 65 cm tall and 54 cm wide;

Propagation: Stem cuttings; rooting in about 3 weeks;

Time to produce finished crop in 3.8-liter pots: About 8 to 10 weeks; vigorous;

Root: Fibrous and freely branching; color creamy white to tan depending on soil type;

Leaves: Simple; opposite; lanceolate; apex narrowly acute; base attenuate; margin micro-dentate; glabrous both adaxial and abaxial; to about 143 mm long by about 49 mm wide, average about 105 mm long and 42 mm wide;

Leaf color: Adaxial expanding nearest RHS 138A and abaxial expanding nearest RHS 146B; mature adaxial nearest RHS NN137B and mature abaxial nearest RHS 147B; lacking anthocyanin expression;

Foliage fragrance: None detected;

Veins: Pinnate; convergent near leaf margin; glabrous adaxial and abaxial, midrib about 1.5 mm wide at base; slightly impressed adaxial and costate abaxial;

Vein color: Adaxial midrib and primary veins nearest RHS 146D; abaxial midrib between RHS 145A and RHS 146D proximally, and distal midrib veins nearest RHS 146C;

Petiole: Flattened; glabrous adaxial and abaxial; about 4 mm long and 3 mm wide;

Petiole color: Nearest RHS 145A adaxial and nearest RHS 146D abaxial;

Stems: Cylindrical; stiff; upright; glabrous, limited branching below flowers; to about 60 cm long and 18 mm diameter near base, average about 46 cm long and 9 mm diameter at base;

Stem color: Proximal portion between RHS 146C and RHS 146D with raised longitudinally striated ridges between RHS 199D and RHS 161B; distal portion nearest RHS 146C; lacking anthocyanin expression;

Nodes: 11 nodes before flowers; average about 4.3 cm apart, greater proximally;

Node color: Color nearest RHS 146D;

Inflorescence: Upright; with up to 14 branched nodes; densely flowering in about the upper 15 cm and about 15 cm wide; about 300 to 500 flowers per branched stem;

Flowers: Perfect; salverform; mostly flat faced; about 33 mm across face and 30 mm long; with fused corolla tube about 27 mm long and 4 mm diameter near face and 2 mm diameter at base; attitude upright to outwardly;

Flower longevity: About 5 days on plant; self-cleaning;

Flower fragrance: Lightly sweet;

Buds one to two days prior to opening: Narrowly clavate to narrowly obovoid; acute apex with narrow tube and rounded base; petals implicate; abaxial corolla tube puberulent, bulb and calyx glabrous;

Bud size: About 27 mm long and 5.5 mm diameter in terminal bulb portion, and 4 mm diameter in corolla tube proximal bulb and base of corolla tube nearest RHS 2.5 mm diameter;

Bud color: Exposed petal bulb portion between RHS 61B and RHS 54A; corolla tube portion between RHS 70A and RHS 72B; calyx base nearest RHS 145D, mid-portion nearest RHS 146B, distally nearest RHS NN137C with proximal margins nearest RHS NN155C and distal margins with moderate of nearest RHS 187B and distal center with heavy blushing of nearest RHS 187B;

Petals: Typically five, rarely six; consisting of limb and basal claw fused into corolla tube; limb obdeltoid to nearly orbicular; apex rounded, margin entire; limbs imbricate about 40 percent; limb glabrous adaxial and abaxial, adaxial corolla tube pubescent in proximal 4 to 6 mm and glabrous distally, abaxial corolla tube puberulent; with no anthocyanins;

Petal size: Limb about 15 mm long and 19 mm wide near middle; tube about 27 mm long and 4 mm diameter near face and 2 mm diameter near base;

Petal color upon first opening:

*Adaxial.*—Limb between RHS 61B and RHS 50A, with center eye rim nearest RHS 64A and center throat nearest RHS N75D; distal 18 mm of corolla tube nearest RHS 72B, proximal 8 mm of corolla tube portion nearest RHS 155D.

*Abaxial.*—Limb between RHS 54A and RHS 54B, corolla tube basal 5 mm nearest RHS NN15B and distally between RHS 70A and RHS 72B.

Petal color upon maturity:

*Adaxial.*—Limb between RHS 61B and RHS 61C, center eye rim nearest RHS 61B and throat nearest RHS 75A, distal 18 mm of corolla tube nearest RHS 77B, proximal 8 mm of corolla tube nearest NN155C.

*Abaxial*.—Limb between RHS 61B and RHS 61C, corolla tube proximal 5 mm nearest RHS NN155B and distally nearest RHS 72B.

Androecium: Typically five;

*Filaments*.—Typically five, adnate to inner corolla to various heights about 21 mm to 26 mm from base; free in the distal 1 mm and 0.2 mm in diameter; color nearest RHS NN155C in free portion and fused portion nearest RHS 76C.

*Anther*.—Five; oblong ellipsoidal; dorsifixed; longitudinal; about 3 mm long by 1 mm wide; color nearest RHS 11C.

*Pollen*.—Abundant; nearly microscopic; color nearest RHS 11C.

Gynoecium: One pistil per flower; 27 mm long;

*Style*.—Cylindrical; about 23 mm long and 0.3 mm diameter when flower is mature; persistent after flower abscission; color nearest RHS 145C, proximally transitioning to nearest RHS 187B distally with flower maturity.

*Stigma*.—Typically trifid in proximal 1 mm long; about 0.3 mm diameter; color nearest RHS 145C.

*Ovary*.—Superior; turbinate; glabrous; lustrous; acute apex and truncate base; about 2 mm long and 1.2 mm diameter at base; color nearest RHS 144B.

Calyx: Campanulate; about 8 mm long and 3 mm across at apex;

Sepals: Typically five, rarely six; linear; glabrous and slightly lustrous adaxial and abaxial glabrous and matte; narrowly acute apex, fused in basal 50 mm, free in distal 3 mm; margin entire; individually about 8 mm long and 1.5 mm wide at fusion;

Sepal color: Adaxial base nearest 145A, margin about 0.5 mm wide nearest RHS 155C with light to moderate blushing of nearest RHS 187B; abaxial base nearest RHS 145B, middle nearest RHS 146C, distally nearest RHS NN137C with moderate to heavily blushing nearest RHS 187B concentrated in center, with margins nearest RHS NN155B;

Peduncle: Glabrous; stiff; upright; cylindrical; highly branched; to 18 cm long and 5 mm diameter; with up to 14 branches at about a 50-degree angle above horizontal, branches to about 2 mm diameter at base and 13 cm long;

Peduncle and branches color: Nearest RHS 146D;

Pedicel: Cylindrical; glabrous; flexible; upright to outwardly; to about 3 mm long and 0.7 mm diameter;

Pedicel color: Between RHS 143C and RHS 146D;

Fruit: Dehiscent, few-seeded capsule, typically 1 seed; fecundity low; flattened ellipsoidal; glabrous; to about 4 mm long and 2.5 mm diameter in middle; color at maturity nearest RHS N200A;

Seeds: Flattened ellipsoidal; glabrous; to 4 mm long, 2.5 mm across and 1.5 mm thick; color nearest RHS 202A;

Hardiness and culture: The new plant grows best with full sun, light moisture and deep drainage; hardy to at least from USDA zone 3 through 8.

Disease and pest resistance: *Phlox* 'Sunset Coral' demonstrates excellent powdery mildew (*Erysiphe cichoracearum*) resistance under conditions that would normally show symptoms. No pest resistance beyond that common for *Phlox* has been observed.

I claim:

1. A new and distinct cultivar of Tall *Phlox, Phlox* plant named 'Sunset Coral', as herein described and illustrated.

* * * * *